United States Patent [19]

Babson

[11] Patent Number: 5,723,092
[45] Date of Patent: Mar. 3, 1998

[54] SAMPLE DILUTION SYSTEM AND DILUTION WELL INSERT THEREFOR

[75] Inventor: Arthur L. Babson, Chester, N.J.

[73] Assignee: DPC Cirrus Inc., Randolph, N.J.

[21] Appl. No.: 672,653

[22] Filed: Jun. 28, 1996

[51] Int. Cl.[6] .................................................. G01N 35/10
[52] U.S. Cl. ........................... 422/63; 422/100; 422/104; 436/49; 436/174; 436/179; 366/213
[58] Field of Search .................... 422/63, 67, 68.1, 422/98, 103, 104; 436/63, 49, 54, 174, 179, 180; 366/213, 220, 232, 228, 307

[56] References Cited

U.S. PATENT DOCUMENTS

| | | | |
|---|---|---|---|
| 3,432,149 | 3/1969 | Stalberg et al. | 366/202 |
| 3,726,144 | 4/1973 | Klein | 422/100 |
| 4,323,537 | 4/1982 | Mody | 422/63 |
| 4,895,453 | 1/1990 | Devlin et al. | 366/219 |
| 4,943,164 | 7/1990 | Ohishi et al. | 366/149 |
| 5,104,231 | 4/1992 | Collier et al. | 466/208 |
| 5,316,726 | 5/1994 | Babson et al. | 422/65 |
| 5,439,645 | 8/1995 | Saralegui et al. | 422/64 |

OTHER PUBLICATIONS

Trade Brochure, entitled "PK310 Fully Automated Enzyme Analyser", a publication of OLYMPUS Biomedical Products Div., Wendenstrasse 14–16, 2 Hamburg 1, Germany, 15 pages, undated.

Primary Examiner—Long V. Le
Attorney, Agent, or Firm—Whitham, Curtis, Whitham & McGinn

[57] ABSTRACT

A sample dilution system including a dilution well waste chamber chamber, a dilution well spinning device, and a dilution well adapted to be controllably rotated by the dilution well spinning device when positioned within the dilution well chamber. The dilution well used in the dilution well system has an outer splash guard and a distal tip to permit facile tube gripping, respectively, and inner fins (baffles) to effect rapid and efficient mixing of the fluid contents of the dilution well.

5 Claims, 1 Drawing Sheet

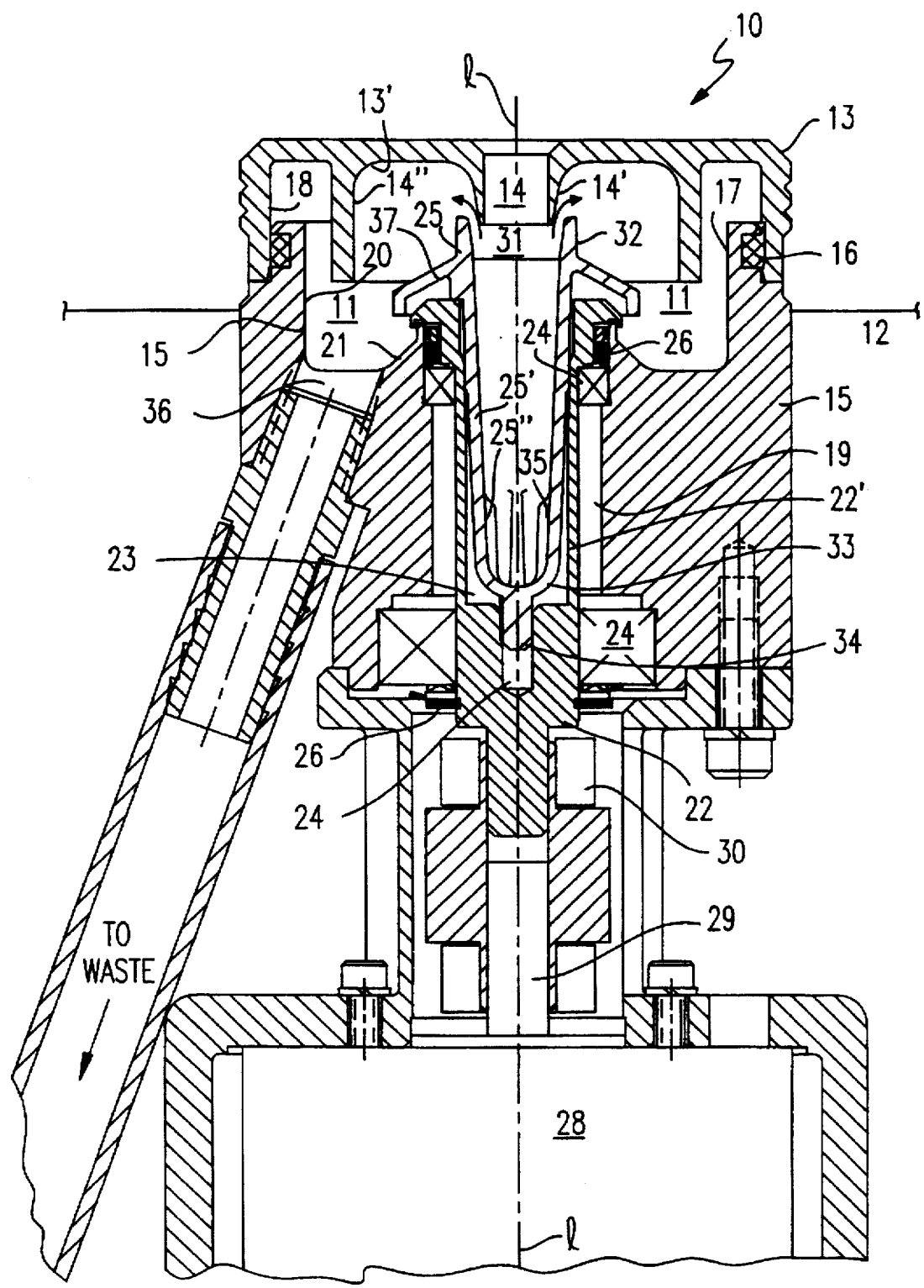

SAMPLE DILUTION SYSTEM AND DILUTION WELL INSERT THEREFOR

BACKGROUND OF THE INVENTION

1. Field of the Invention

The invention is generally relates to a sample dilution system, which is particularly well-suited for the dilution of specimens in an automated chemical or immunoassay analyzer. The invention also relates to a dilution well insert that can be used in the inventive sample dilution system.

2. Description of the Prior Art

An immunoassay is a well known laboratory method used to determine the amount of an analyte in a sample such as plasma or urine. It is based on the interaction of antibodies with antigens, and because of the degree of selectivity for the analyte (either antigen or antibody), an immunoassay can be used to quantitatively determine very low concentrations of drugs, hormones, polypeptides, or other analyte compounds found in a test sample. For many years, immunoassays were performed by hand by trained laboratory technicians.

Recently, many companies have begun producing automated immunoassay analyzers. Automating the immunoassay procedures can be onerous because of the large number of steps needed to be executed. For example, in a conventional scheme, a sample is mixed with a reagent and a solid support having a bound antigen or antibody, the sample is incubated such that the corresponding antigen or antibody in the sample and a labeled antigen or antibody provided in the reagent can be bound to the antigen or antibody on the solid support, then the solid support is thoroughly washed and the label (fluorescent, radioactive, chemiluminescent, or the like) is detected by an appropriate mechanism, and finally the analyte of interest (antigen or antibody) is quantified from the detected label. Solid-phase bead heterogenous enzyme immunoassay by sandwich methodology is one conventional approach to conducting such assays.

Most of today's automated immunoassay analyzers are designed for "walk away" operation, where the technician loads sample containing tubes onto a carousel and presses a start button. Thereafter, the automated immunoassay analyzer mixes appropriate reagents (often stored aboard the analyzer) with the sample, performs incubating and washing operations, detects the label, and computes the quantity of analyte in the sample from the detected label and stored calibration curves. The entire operation is typically done under computer control, and in some automated immunoassay analyzers, bar coding is used to identify the sample under test. The results of the immunoassays are typically output onto computer paper for inspection by the technician, or monitored and displayed in real time as described in U.S. Pat. No. 5,316,726.

In immunoassays, it is often necessary or desired to dilute a sample prior to assay with a quantity of a diluent such as deionized water. In prior immunoassay systems, two approaches are known for diluting a sample. In one prior approach, the sample and diluent had to be manually mixed by a technician before being transferred to a assay tube holding the solid support having a bound antibody or antigen, before incubation. In a second approach, the prior art has used non-reusable dilution cups or other disposables for sample dilution. These approaches, however, are wasteful in terms of cup handling and disposal, or are labor demanding which lowers the level of automation in the system.

SUMMARY OF THE INVENTION

It is an object of this invention to provide a sample dilution system capable of rapid mixture of quantities of specimen, diluent and/or other fluids to form a homogenous fluid mixture.

It is a further object of this invention to provide a sample dilution system having a re-useable sample well configuration well-suited for dilution of fluid samples, and cleaning.

It is yet another object of the invention to provide an improved dilution well insert that can be facilely used in the sample dilution system.

According to an embodiment of the invention, a high performance sample dilution system is provided. In the sample dilution system of this invention, there is a unique combination including a dilution well waste chamber, a dilution well spinning means located in the base of the chamber, and a re-useable dilution well removably nested in the spinning means that is used to mix and dilute liquid samples by rotary motion imparted by the spinning means.

The dilution well waste chamber is an enclosure defined by a stationary chamber body having side walls and a bottom, and a removable dilution well cover having a central opening. A drainage port is provided in or near the bottom of the chamber to collect and permit drainage of fluid flung out of the dilution well during a dilution well cleaning mode. A centrally located opening through the bottom of the chamber body houses a rotatable spindle means. The spindle includes a hollow sleeve sized to allow the dilution well to be nested and interfit inside the spindle such that the dilution well will travel in rotation with the spindle. The dilution well, such as a mixing tube, is nested in the rotatable spindle during a dilution and mixing mode and a cleaning (high speed spinning) mode.

The dilution well is preferably a separate piece or insert that can be inserted or removed from a nested position in the spindle. The dilution well is configured so that it can be controllably rotated by the spindle when positioned (nested) within the spindle.

In one embodiment, the dilution well is a tube insert having an inner surface defining a tubular structure including an elongated hollow cylinder formed with tapered tube walls extending from a closed lower end to an opening at an upper end. The upper end provides a tube access opening and the closed lower end is formed with a plurality of inward projecting fins (baffles) integral with the inner tube walls. The integral interior fins (i.e., baffles) help provide rapid and efficient mixing of fluid contents of the dilution well. The outer surface of the dilution well includes a flange structure located below the upper end of the tube which acts as a splash guard or apron to protect the spindle and its bearings, and the motor components, from water expelled from the dilution well during tube cleaning. The flange is integral with and extends laterally from the outer surface of the upper end of the tube. The outer surface of the dilution well also includes an integral distal tip extending co-axially with the longitudinal axis of the dilution well, and the distal tip fits into a recess formed in the base of the spindle to provide enhanced gripping of the dilution well.

Fluid materials, such as the sample, diluent and/or water can be added to the dilution well, when nested in the aforementioned spindle by pipette with access to the dilution well chamber and mouth of the dilution well made possible by a central opening provided in a removable dilution well cover attached to the top of the waste chamber. Therefore, the inventive sample dilution system is a water-tight enclosure other than for a drainage port and an aperture defined in the removable cover having a size effective to permit reciprocal insertion and withdrawal of a pipette. The spindle is mechanically connected to drive means capable of effecting rotation of the spindle, and hence, the nested dilution well. For instance, the spindle can be rotated by a motor via a flexible coupling. Bearings and water tight seals preferably are used to exclude water from the spindle and motor components.

The motor used for driving the spindle, and a dilution well nested therein, in rotation preferably is capable of adjustment between intermittent and continuous operation modes. The intermittent mode being useful during mixing of the contents in the dilution well. By intermittently energizing the dilution well in pulses, the fluid contents of the tube are vigorously inter-mixed as encouraged by the fins or baffles provided on the inner sidewalls of the dilution well. On the other hand, the continuous high speed spinning mode is used to clean out any excess fluid contents from the tube remaining after a mixed sample has been withdrawn and transferred to an assay tube for beginning the actual sample analysis. During high speed rotation, left-over fluids in the tube creep up the interior walls of the tube until they reach the mouth of the tube at which point the waste fluids are flung out of the tube and against the inside walls of the dilution well waste chamber. The expelled fluids drain by gravity into the lower basin of the waste chamber and out of a drainage port into waste. Further tube cleaning can be accomplished by the repetitive additions of wash water to the tube during, or followed by, spinning out the wash fluids.

The sample dilution system of this invention makes it possible to enhance the integrity and validity of assay test results by providing means to prepare a homogenous pre-dispersion of a sample in deionized water or other diluent prior to introduction of the sample into a reaction tube. The inventive sample dilution system also enables a sample to be diluted in a re-useable well which avoids the use of single use mixing cups or manual mixing by technicians.

BRIEF DESCRIPTION OF THE DRAWING

The foregoing and other objects, aspects and advantages will be better understood from the following detailed description of the preferred embodiments of the invention with reference to the drawing, in which:

The FIGURE is a cross-sectional view of a sample dilution system of the invention.

DETAILED DESCRIPTION OF THE PREFERRED EMBODIMENTS OF THE INVENTION

The sample dilution system of the present invention can be used as a subsystem of an analytical instrument intended to produce reportable assay results through the processing of specimens and various other components of the chemistry system. The latter mentioned processing involves the control and timing of various internal operations as well as the acquisition and processing of data generated internally or through interaction with an external computer system such as LIS. The analytic instrument is an integrated electromechanical apparatus which processes specimens in order to generate test results. It is comprised of all the mechanical hardware, electronic hardware and software required to perform chemical or immunoassays.

Referring now to the drawings, and more particularly to the FIGURE, there generally is shown a sample dilution system 10 of the present invention. Specimens may be diluted prior to assay either at the request of the user or automatically. This is accomplished via mixing of a specimen aliquot and a quantity of a diluent, such as a protein diluent or deionized water, in the sample dilution system 10. The dilution well waste chamber 11 is an enclosure defined by chamber walls 20, 21 of chamber body 15 and a removable dilution well cover 13. As illustrated, the waste chamber 11 can be conveniently formed at least partly recessed in a work station table top 12, such as of an immunoassay instrument. The removable dilution well cover 13 has a central opening 14 for pipette access. Concentric projections 14' and 14" extending from the lower side 13' of the cover 13 help direct a pipette into the mouth 31 of the dilution well 25 and channel waste fluids during well cleaning, respectively. The chamber body 15 includes flange 17 retaining O-ring 16 which forms a seal with the rim 18 of the cover 13.

The chamber body 15 is stationary and defines inner sidewalls 20, and bottom 21 having a drainage port 22 and a centrally located opening 19. The central opening 19 houses a rotatable dilution well spindle 22. Bearings 24 are provided between the stationary chamber body 15 and the rotatable spindle means 22. The spindle 22 includes a hollow sleeve 22 defining a recess 23 sized to allow the dilution well 25 to be nested and frictionally interfit inside the spindle 22 such that the dilution well 25 will travel in rotation with the spindle 22. The spindle can be driven in rotation by adjustable motor 28 having drive shaft 29 mechanically connected to spindle 22 via a coupling 30. Teflon seals 26 are also preferably provided between the chamber body 15 and spindle 22, as shown, to provide a water-tight system that seals the bearings 24 and motor 28/drive 29 from contact with fluids. The rotatable spindle 22 can be stainless steel or another material that is corrosion resistant in the presence of water.

The dilution well 25, shown as a test tube-like insert configuration in the FIGURE, is nested in the rotatable spindle 22 during a dilution and mixing mode and a cleaning high speed spinning mode, but it is a separate removable piece from the system in a preferred embodiment. As shown in the FIGURE, the spindle 22 and nested dilution well 25 are centered in the chamber 11 relative to imaginary longitudinal axis l. Preferably, the dilution well 25 is a non-wettable material, such as polypropylene, to facilitate water removal from the well 25. In an alternate arrangement, the dilution well 25 can be formed integrally with the spindle 22.

The dilution well 25, as illustrated as a tube insert in the FIGURE, includes an elongate tapered, hollow cylindrical section 25' having an opening 31 at its upper end 32 and terminating in a closed lower end 33. The tapering or draft angle of the inner surface 25" of the dilution well tube 25 preferably is about 2° such that the tube's inner walls 25" slope slightly outward away from axis l. The taper facilitates creep of the waste fluids out of the bottom of the tube 25 up to the opening 31 during a high speed cleaning mode. A distal tip 34 axially extends from the lower tube end 33 and the tip 34 conformably fits within the gripping recess 24 formed in spindle 22 which effectively forms a grip by the spindle 22 on the dilution well 25. The upper end 32 of the dilution well 25 also has an integral flange 37 which extends radially outward in all directions and it serves as a splash guard that covers and helps protect spindle 22 and motor 28/drive 29 system from fluid contact during the execution of the cleaning mode of the dilution system 10, described in more detail elsewhere herein. The dilution well 25 also includes a plurality of fins or baffles 35 integrally attached to the inner walls 25" of the dilution well 25 which project inward and effectively act as agitators during fluid mixing and dilution. For example, about 3-5 equidistantly spaced fins 35 can be used. The sample and diluent can be filled in the dilution well 25 to a depth that exceeds the height of the fins 35. A dilution well tube 25 having these features can be formed of plastic material by use of conventional plastic molding techniques.

The spindle drive system preferably is capable of adjustment between intermittent and continuous operation modes; the intermittent mode being useful during mixing of the contents in the dilution well. By intermittently energizing the motor 28 in pulses, the fluid contents of the tube are vigorously inter-mixed as encouraged by the fins or baffles provided on the inner sidewalls of the dilution well. On the other hand, the continuous high speed spinning mode is used to clean out the remaining excess fluid contents from the tube after the mixed sample has been withdrawn and transferred to an assay tube for beginning the actual sample analysis. During high speed rotation, left-over fluids in the tube creep up the interior walls of the tube until they reach the mouth of the tube at which point the waste fluids are flung out of the tube and against the inside walls of the dilution well waste chamber. The expelled fluids drain by gravity into the lower basin of the waste chamber and out of a drainage port into waste. Further tube cleaning can be accomplished by the repetitive additions of wash water to the tube during, or followed by, spinning out the wash fluids.

An adjustable spin motor 28 preferably is used that is capable of precision control as to its motor speed and/or capability for relatively brief and instantaneous energization periods. For instance, to effect mixing and dilution of a sample and specimen in the nested dilution well, the motor preferably is "pulsed" to achieve rapid mixing, i.e., the motor is energized for about 100 milliseconds to put the spindle (and dilution well) in rotation, and then de-energized for about 400 milliseconds such that the spindle de-accelerates and stops rapidly due to friction, and then repeating the energization/de-energization cycle at least several times. The dilution well contents are generally pulsed in this manner about 6–8 times; although 3–4 pulses typically has been found adequate for homogenous mixing to be achieved. This scheme effectively causes alternating acceleration/de-acceleration of the dilution well 25 in rotation at low average rpm's such that the fluid contents are well agitated yet without causing the fluids to creep up the inner walls 25" of the dilution well 25 and be prematurely flung out and spilled from the dilution well 25. The pulsed (stop-and-go) tube rotations together with the agitator-like action of the sample tube fins or baffles 35 effectively mixes the sample and diluent held in the dilution well 25 into a homogenous mixture.

A sample pipette, which interacts with but does not form part of the dilution well system per se, can then be used to extract dilute sample from the dilution well 25 and transfer a fraction of the diluted sample to a reaction tube (not shown) for assay. Once the dilute sample is extracted, the dilution well tube 25 is driven in continuous rotation at high speed to cause any residual waste fluids to creep up the inner walls 25" of the dilution well 25 to opening 31 where the fluids are flung out of the tube 25 as indicated by the arrows, which contents are captured within the dilution well waste chamber 11 and drained out of drainage port 36 at the base 21 of waste chamber 11. Wash water can be pipetted into the dilution well 25 through aperture 31 and spun out, once or several times in succession, to further clean the dilution well before introduction, dilution, and mixing of the next sample therein. For most high speed spin removal operations, the tube spin rate will generally range from about 3,000 to about 10,000 rpm. The expelled sample, diluent or other waste fluids drain by gravity into the lower reaches of the chamber 11 and are withdrawn for disposal via drainage port 36.

The sample dilution system of this invention can be used as a subsystem of an immunoanalyzer used to perform immunoanalysis on a sample of interest in which the sample can be diluted with diluent or water and mixed into a homogenous solution in the dilution well system of this invention, and then withdrawing a fraction of the mixed sample via pipette and depositing same in a reaction tube (already containing the coated bead) in which a liquid reagent is also added. The mixture of reagent and diluted sample can then be processed according to conventional techniques such as by incubating and agitating the mixture, washing the bead, and then having a substrate (e.g., chemiluminescent) added and incubated for quantitation of analyte (e.g., by reaction tube light output measurement).

When the inventive dilution well system is used in an immunoanalyzer instrument, it is possible to provide user defined dilution factors for the sample prior to analysis and to allow adjustment of the amount of sample dilution in response to prior results where samples give results exceeding the valid measurement limits.

While the invention has been described in terms of its preferred embodiments, those skilled in the art will recognize that the invention can be practiced with modification within the spirit and scope of the appended claims.

I claim:

1. A re-useable sample dilution system comprising, in combination:

a dilution well waste chamber defined by (a) a chamber body having inner sidewalls and a bottom defining a space, wherein said bottom includes a drainage port and a centrally located opening, and (b) a dilution well cover having a central hole, said dilution well cover being removably fitted upon said chamber body to cover said space;

a dilution well, including:
an elongated hollow cylinder having inside walls, an upper end and a lower end, said upper end having an opening and said lower end having a plurality of inward projecting fins integral with said inside tube walls;

a dilution well spinning means, including:
a holding means for conformably receiving and supporting said dilution well,
a drive means capable of effecting rotation of said holding means and said dilution well, wherein said drive means includes a motor, and said holding means comprises a spindle where said motor controllably drives said spindle in rotation, and said spindle comprising a hollow sleeve defining a recess sized to permit nesting of said dilution well inside said spindle whereby said dilution well is capable of traveling in rotation with said spindle.

2. The sample dilution system of claim 1, wherein said motor is capable of intermittent and continuous operation.

3. The sample dilution system of claim 1, wherein said dilution well comprises a tube.

4. The sample dilution system of claim 3, wherein said tube, includes:
a solid distal tip end extending axially from said lower end of said tube, and
a splash guard flange integral with and extending laterally outward from said upper end of said tube.

5. The sample dilution system of claim 1, wherein said chamber body further includes a drainage hole in said side walls or bottom to collect and drain fluid.

* * * * *